United States Patent
Policker et al.

(10) Patent No.: US 8,831,729 B2
(45) Date of Patent: *Sep. 9, 2014

(54) SYSTEMS AND METHODS FOR TREATING GASTROESOPHAGEAL REFLUX DISEASE

(75) Inventors: Shai Policker, Tenafly, NJ (US); Virender K. Sharma, Paradise Valley, AZ (US)

(73) Assignee: EndoStim, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/447,168

(22) Filed: Apr. 14, 2012

(65) Prior Publication Data

US 2012/0265103 A1    Oct. 18, 2012

Related U.S. Application Data

(63) Continuation-in-part of application No. 13/041,063, filed on Mar. 4, 2011.

(60) Provisional application No. 61/475,368, filed on Apr. 14, 2011.

(51) Int. Cl.
*A61N 1/36* (2006.01)
*A61N 1/00* (2006.01)
*A61N 1/372* (2006.01)
*G06F 19/00* (2011.01)

(52) U.S. Cl.
CPC ......... *A61N 1/36007* (2013.01); *A61N 1/37205* (2013.01); *A61N 1/37282* (2013.01); *A61N 1/00* (2013.01); *G06F 19/34* (2013.01)
USPC .......................................................... 607/40

(58) Field of Classification Search
CPC ..................... A61N 1/36007; A61N 1/36085
USPC ............................................................ 607/40
See application file for complete search history.

(56) References Cited

U.S. PATENT DOCUMENTS

| 4,612,934 A | 9/1986 | Borkan |
|---|---|---|
| 5,117,827 A | 6/1992 | Stuebe |

(Continued)

FOREIGN PATENT DOCUMENTS

| WO | 9853878 | 12/1998 |
|---|---|---|
| WO | 0061223 | 10/2000 |

(Continued)

OTHER PUBLICATIONS

Christensen et al., 'Physiologic Specialization at Esophagogastric Junction in Three Species', American Journal of Physiology, vol. 225, No. 6, Dec. 1973, 1265-1270.

(Continued)

*Primary Examiner* — Joseph Dietrich
(74) *Attorney, Agent, or Firm* — Novel IP

(57) ABSTRACT

Systems and methods for treating gastroesophageal reflux disease (GERD) includes minimally invasively implanting a stimulating device in a patient's esophagus in the region proximate the lower esophageal sphincter (LES). The patient is provided with a questionnaire related to his disease via an online service. The questionnaire is accessed on a mobile device, such as a cell phone, or on a computer with network access. The data from the sensors and the answers from the questionnaire are analyzed together by a health care provider using the online service. The data and answers are used to program the stimulating device, via the mobile device or computer, to optimize treatment.

17 Claims, 4 Drawing Sheets

(56) References Cited

U.S. PATENT DOCUMENTS

| | | |
|---|---|---|
| 5,231,988 A | 8/1993 | Wernicke |
| 5,263,480 A | 11/1993 | Wernicke |
| 5,292,344 A | 3/1994 | Douglas |
| 5,423,872 A | 6/1995 | Cigaina |
| 5,540,730 A | 7/1996 | Terry |
| 5,690,691 A | 11/1997 | Chen |
| 5,716,385 A | 2/1998 | Mittal |
| 5,836,994 A | 11/1998 | Bourgeois |
| 5,861,044 A | 1/1999 | Crenshaw |
| 6,041,258 A | 3/2000 | Cigaina |
| 6,091,992 A | 7/2000 | Bourgeois |
| 6,097,984 A | 8/2000 | Douglas |
| 6,216,039 B1 | 4/2001 | Bourgeois |
| 6,285,897 B1 | 9/2001 | Kilcoyne |
| 6,321,124 B1 | 11/2001 | Cigaina |
| 6,381,495 B1 | 4/2002 | Jenkins |
| 6,449,511 B1 | 9/2002 | Mintchev |
| 6,510,332 B1 | 1/2003 | Greenstein |
| 6,587,719 B1 | 7/2003 | Barrett |
| 6,591,137 B1 | 7/2003 | Fischell |
| 6,611,715 B1 | 8/2003 | Boveja |
| 6,615,084 B1 | 9/2003 | Cigaina |
| 6,678,561 B2 | 1/2004 | Forsell |
| 6,749,607 B2 | 6/2004 | Edwards |
| 6,754,536 B2 | 6/2004 | Swoyer |
| 6,760,626 B1 | 7/2004 | Boveja |
| 6,826,428 B1 | 11/2004 | Chen |
| 6,832,114 B1 | 12/2004 | Whitehurst |
| 6,879,859 B1 | 4/2005 | Boveja |
| 6,901,295 B2 | 5/2005 | Sharma |
| 6,947,792 B2 | 9/2005 | Ben-Haim |
| 7,006,871 B1 | 2/2006 | Darvish |
| 7,016,735 B2 | 3/2006 | Imran |
| 7,054,689 B1 | 5/2006 | Whitehurst |
| 7,054,690 B2 | 5/2006 | Imran |
| 7,076,305 B2 | 7/2006 | Imran |
| 7,076,306 B2 | 7/2006 | Marchal |
| 7,087,053 B2 | 8/2006 | Vanney |
| 7,114,502 B2 | 10/2006 | Schulman |
| 7,120,498 B2 | 10/2006 | Imran |
| 7,146,216 B2 | 12/2006 | Bumm |
| 7,167,750 B2 | 1/2007 | Knudson |
| 7,177,693 B2 | 2/2007 | Starkebaum |
| 7,200,443 B2 | 4/2007 | Faul |
| 7,263,405 B2 | 8/2007 | Boveja |
| 7,299,091 B2 | 11/2007 | Barrett |
| 7,310,557 B2 | 12/2007 | Maschino |
| 7,340,306 B2 | 3/2008 | Barrett |
| 7,343,201 B2 | 3/2008 | Mintchev |
| 7,444,183 B2 | 10/2008 | Knudson |
| 7,620,454 B2 | 11/2009 | Dinsmoor |
| 7,702,394 B2 | 4/2010 | Imran |
| 7,702,395 B2 | 4/2010 | Towe |
| 7,729,771 B2 | 6/2010 | Knudson |
| 7,734,355 B2 | 6/2010 | Cohen |
| 7,738,961 B2 | 6/2010 | Sharma |
| 7,742,818 B2 | 6/2010 | Dinsmoor |
| 7,794,425 B2 | 9/2010 | Gobel |
| 7,835,796 B2 | 11/2010 | Maschino |
| 7,899,540 B2 | 3/2011 | Maschino |
| 7,914,468 B2 | 3/2011 | Shalon |
| 7,962,214 B2 | 6/2011 | Byerman |
| 8,160,709 B2 | 4/2012 | Soffer |
| 8,282,561 B2 | 10/2012 | Towe |
| 8,447,403 B2 | 5/2013 | Sharma |
| 8,447,404 B2 | 5/2013 | Sharma |
| 8,452,407 B2 | 5/2013 | Whitehurst |
| 8,543,210 B2 | 9/2013 | Sharma |
| 8,712,529 B2 | 4/2014 | Sharma |
| 8,712,530 B2 | 4/2014 | Sharma |
| 2001/0041831 A1 | 11/2001 | Starkweather |
| 2002/0161414 A1 | 10/2002 | Flesler |
| 2002/0165589 A1 | 11/2002 | Imran |
| 2003/0014086 A1* | 1/2003 | Sharma ............ 607/40 |
| 2003/0078633 A1 | 4/2003 | Firlik |
| 2003/0144708 A1 | 7/2003 | Starkebaum |
| 2004/0012088 A1 | 1/2004 | Fukasawa |
| 2004/0015201 A1 | 1/2004 | Greenstein |
| 2004/0024428 A1 | 2/2004 | Barrett |
| 2004/0039427 A1 | 2/2004 | Barrett |
| 2004/0044376 A1 | 3/2004 | Flesler |
| 2004/0059393 A1 | 3/2004 | Policker |
| 2004/0073453 A1 | 4/2004 | Nenov |
| 2004/0116977 A1 | 6/2004 | Finch |
| 2004/0167583 A1 | 8/2004 | Knudson |
| 2004/0172088 A1 | 9/2004 | Knudson |
| 2004/0186544 A1 | 9/2004 | King |
| 2004/0193229 A1 | 9/2004 | Starkebaum |
| 2004/0243182 A1 | 12/2004 | Cohen |
| 2005/0049655 A1 | 3/2005 | Boveja |
| 2005/0065571 A1 | 3/2005 | Imran |
| 2005/0070974 A1 | 3/2005 | Knudson |
| 2005/0075678 A1 | 4/2005 | Faul |
| 2005/0090873 A1 | 4/2005 | Imran |
| 2005/0131486 A1 | 6/2005 | Boveja |
| 2005/0137643 A1 | 6/2005 | Mintchev |
| 2005/0137644 A1 | 6/2005 | Boveja |
| 2005/0143787 A1 | 6/2005 | Boveja |
| 2005/0149141 A1 | 7/2005 | Starkebaum |
| 2005/0149142 A1 | 7/2005 | Starkebaum |
| 2005/0149146 A1 | 7/2005 | Boveja |
| 2005/0222637 A1 | 10/2005 | Chen |
| 2005/0251219 A1 | 11/2005 | Evans |
| 2006/0036293 A1 | 2/2006 | Whitehurst |
| 2006/0064037 A1 | 3/2006 | Shalon |
| 2006/0074459 A1 | 4/2006 | Flesler |
| 2006/0095077 A1 | 5/2006 | Tronnes |
| 2006/0106442 A1 | 5/2006 | Richardson |
| 2006/0116736 A1 | 6/2006 | DiLorenzo |
| 2006/0167498 A1 | 7/2006 | DiLorenzo |
| 2006/0206160 A1 | 9/2006 | Cigaina |
| 2006/0218011 A1 | 9/2006 | Walker |
| 2006/0247722 A1 | 11/2006 | Maschino |
| 2007/0016274 A1 | 1/2007 | Boveja |
| 2007/0106337 A1 | 5/2007 | Errico |
| 2007/0162084 A1 | 7/2007 | Chen |
| 2007/0162085 A1 | 7/2007 | DiLorenzo |
| 2007/0238942 A1 | 10/2007 | Baylor |
| 2007/0239248 A1 | 10/2007 | Hastings |
| 2008/0021512 A1 | 1/2008 | Knudson |
| 2008/0039904 A1 | 2/2008 | Bulkes |
| 2008/0086179 A1 | 4/2008 | Sharma |
| 2008/0147137 A1 | 6/2008 | Cohen |
| 2008/0154191 A1 | 6/2008 | Gobel |
| 2008/0195171 A1 | 8/2008 | Sharma |
| 2008/0208355 A1 | 8/2008 | Stack |
| 2009/0020406 A1 | 1/2009 | Nirmalakhandan |
| 2009/0030475 A1 | 1/2009 | Brynelsen |
| 2009/0069803 A1 | 3/2009 | Starkebaum |
| 2009/0132001 A1 | 5/2009 | Soffer |
| 2009/0204063 A1 | 8/2009 | Policker |
| 2009/0264951 A1 | 10/2009 | Sharma |
| 2009/0281553 A1 | 11/2009 | Kalloo |
| 2010/0198039 A1 | 8/2010 | Towe |
| 2010/0324432 A1 | 12/2010 | Bjorling |
| 2011/0004266 A1 | 1/2011 | Sharma |
| 2011/0071589 A1 | 3/2011 | Starkebaum |
| 2011/0295335 A1 | 12/2011 | Sharma |
| 2011/0295336 A1 | 12/2011 | Sharma |
| 2011/0307027 A1 | 12/2011 | Sharma |
| 2011/0307028 A1 | 12/2011 | Sharma |
| 2012/0232610 A1 | 9/2012 | Soffer |
| 2012/0265103 A1 | 10/2012 | Policker |
| 2013/0035740 A1 | 2/2013 | Sharma |
| 2013/0090551 A1 | 4/2013 | Sharma |
| 2013/0178912 A1 | 7/2013 | Sharma |
| 2013/0231660 A1 | 9/2013 | Edwards |
| 2014/0018657 A1 | 1/2014 | Sharma |
| 2014/0088664 A1 | 3/2014 | Sharma |

FOREIGN PATENT DOCUMENTS

| | | |
|---|---|---|
| WO | 0061223 A1 | 10/2000 |
| WO | 0061224 | 10/2000 |

(56) References Cited

FOREIGN PATENT DOCUMENTS

| WO | 0061224 A1 | 10/2000 |
|---|---|---|
| WO | 0243467 | 6/2002 |
| WO | 0243467 A2 | 6/2002 |
| WO | 2005051486 A1 | 9/2005 |
| WO | 2007137026 | 11/2007 |
| WO | 2009114008 A1 | 9/2009 |
| WO | 2010027963 | 3/2010 |
| WO | 2010135634 | 11/2010 |
| WO | 2012151449 | 11/2012 |
| WO | 2014032030 | 2/2014 |

OTHER PUBLICATIONS

Ellis, et al., 'The Prevention of Experimentally Induced Reflux by Electrical Stimulation of the Distal Esophagus', American Journal of Surgery, vol. 115, Apr. 1968, 482-487.
Gonzalez et al., 'Different Responsiveness of Excitatory and Inhibitory Enteric Motor Neurons in the Human Esophagus to Electrical Field Stimulation and to Nicotine', Am J Physiol Gastrointest Liver Physiol, 287:G299-G306, 2004.
Kahrilas et al., 'Impact of Fundoplication on Bolus Transit Across Esophagogastric Junction', American Physiological Society, 1998, 1386-1393.
Kamath et al., 'Neurocardiac and Cerebral Responses Evoked by Esophageal Vago-Afferent Stimulation in Humans: Effects of Varying Intensities', Cardiovascular Research, 40 (1998) 591-599.
Lund et al., 'Electrical Stimulation of Esophageal Smooth Muscle and Effects of Antagonists', American Journal of Physiology, vol. 217, No. 5, Nov. 1969, 1369-1374.
Stein et al., 'Three-dimensional Imaging of the Lower Esophageal Sphincter in Gastroesophageal Reflux Disease,' Annual Meeting of the American Surgical Association, Apr. 11-13, 1991, 374-383.
International Search Report for PCT/US2007/068907.
International Search Report for PCT/US2012/036408, Aug. 17, 2012.
International Search Report for PCT/US2008/053780, Jun. 8, 2009.
Summary of Neurostimulation Systems Features, Advanced Neuromodulation Systems (ANS) home page, accessed on May 31, 2007 at http://web.archive.org/web/20040211224857/www.ans-medical.com/patients/WhichSystemIsBest/SumOfNeurostimulation.html.
International Search Report for PCT/US2008/056479, Aug. 20, 2008.
International Search Report for PCT/US2011/027243, Jul. 8, 2011.
International Search Report for PCT/US12/053576, Dec. 24, 2012.
International Search Report for PCT/US2012/033695, Aug. 7, 2012.
EPO Search Report EP09704463, Jan. 10, 2011, Virender K. Sharma.
International Search Report for PCT/US2013/056520, Apr. 4, 2014.
Clarke et al., 'An endoscopically implantable device stimulates the lower esophageal sphincter on demand by remote control: a study using a canine model', Endoscopy 2007; 39: 72-76.
Xing et al., 'Gastric Electrical Stimulation Significantly Increases Canine Lower Esophageal Pressure' Gastroenterology 122: May Issue, A579, 2003. Presented as a poster at Digestive Disease Week in Orlando, FL on Monday, May 19, 2003.
Xing et al, 'Gastric Electrical Stimulation (GES) with Parameters for Morbid Obesity Elevates Lower Esophageal Sphincter (LES) Pressure in Conscious Dogs'; Obesity Surgery; 15; 2005; pp. 1321-1327.
Cigaina, Valerio; Long-term Follow-Up of Gastric Stimulation for Obesity: The Mestre 8-Year Experience; Obesity Surgery; 14; 2004; S14-22.
Xing et al, 'Gastric Electrical Stimulation Significantly Increases Canine Lower Esophageal Sphincter Pressure'; Digestive Diseases and Sciences; vol. 50, No. 8 (Aug. 2005), pp. 1481-1487.
Sanmiguel et al, 'Effect of electrical stimulation of the LES on LES pressure in a canine model'; Am J Physiol Gastrointest Live Physiol; 295: 389-394; 2008.
Clarke et al,. 'An Endoscopic Implantable Device Stimulates the LES On-Demand By Remote Control in a Canine Model'; Gastrointestinal Endoscopy, Volum 63, No. 5; 2006, AB103, 759.
Kantsevoy et al., 'An Endoscopically Implantable On-Demand Stimulator Is Successful in Increasing Lower Esophageal Sphincter Pressure in a Porcine Model'; Gastrointestinal Endoscopy, vol. 61, No. 5: 2005, AB79, 222.
Xing et al., 'Gastric Electrical Stimulation Significantly Increases Canine Lower Esophageal Pressure' M1811 Cleveland, OH, May 19, 2003.

\* cited by examiner

SYSTEMS AND METHODS FOR TREATING GASTROESOPHAGEAL REFLUX DISEASE

CROSS REFERENCE

The present application relies on U.S. Provisional Application No. 61/475,368, filed on Apr. 14, 2011 and entitled "Electrical Stimulation Systems and Methods", which is incorporated herein by reference. The present application is also a continuation in part of U.S. patent application Ser. No. 13/041,063, published as U.S. Patent Publication No. 20110307027 ("'027 Publication"), entitled "Device and Implantation System for Electrical Stimulation of Biological Tissues", filed on Mar. 4, 2011, which is also incorporated herein by reference. The '027 Publication claims priority from U.S. Patent Provisional Nos. 61/444,849, filed on Feb. 21, 2011, 61/422,967, filed on Dec. 14, 2010, 61/414,378, filed on Nov. 16, 2010, 61/384,105, filed on Sep. 17, 2010, 61/371,146, filed on Aug. 5, 2010, 61/328,702, filed on Apr. 28, 2010, 61/318,843, filed on Mar. 30, 2010, and 61/310,755, filed on Mar. 5, 2010.

FIELD

This invention relates generally to a method and apparatus for electrical stimulation of the biological systems. More particularly, this invention relates to methods and systems for treating gastroesophageal reflux disease (GERD) by implanting an electrical stimulation device using laparoscopic or endoscopic techniques, capturing an eating event and detecting eating, using an implantable electrical stimulation device, enabling a patient to interface with an implanted stimulation device, and applying predefined treatment processes.

BACKGROUND

Gastro-esophageal reflux disease (GERD) is a common problem and is expensive to manage in both primary and secondary care settings. This condition results from exposure of esophageal mucosa to gastric acid and bile as the gastro-duodenal content refluxes from the stomach into the esophagus. The acid and bile damages the esophageal mucosa resulting in heartburn, ulcers, bleeding, and scarring, and long term complications such as Barrett's esophagus (pre-cancerous esophageal lining) and adeno-cancer of the esophagus.

Lifestyle advice and antacid therapy are advocated as first line treatment for the disease. However, since most patients with moderate to severe cases of GERD do not respond adequately to these first-line measures and need further treatment, other alternatives including pharmacological, endoscopic, and surgical treatments are employed.

The most commonly employed pharmacological treatment is daily use of H2 receptor antagonists (H2RAs) or proton-pump inhibitors (PPIs) for acid suppression. Since gastro-esophageal reflux disease usually relapses once drug therapy is discontinued, most patients with the disease, therefore, need long-term drug therapy. However, daily use of PPIs or H2RAs is not universally effective in the relief of GERD symptoms or as maintenance therapy. Additionally, not all patients are comfortable with the concept of having to take daily or intermittent medication for the rest of their lives and many are interested in nonpharmacological options for managing their reflux disease.

Several endoscopic procedures for the treatment of GERD have been tried. These procedures can be divided into three approaches: endoscopic suturing wherein stitches are inserted in the gastric cardia to plicate and strengthen the lower esophageal sphincter, endoscopic application of energy to the lower esophagus, and injection of bulking agents into the muscle layer of the distal esophagus. These procedures, however, are not without their risks, besides being technically demanding and involving a long procedure time. As a result, these procedures have largely been discontinued.

Open surgical or laparoscopic fundoplication is also used to correct the cause of the disease. However, surgical procedures are associated with significant morbidity and small but not insignificant mortality rates. Moreover, long-term follow-up with patients treated by surgery suggests that many patients continue to need acid suppressive medication. There is also no convincing evidence that fundoplication reduces the risk of esophageal adenocarcinoma in the long term.

While electrical stimulation has been suggested for use in the treatment of GERD, an effective electrical stimulation system has yet to be demonstrated. In particular, the prior art teaches that effective electrical stimulation requires active, real-time sensing for a patient's swallow and, based on a sensed swallow, to immediately cease stimulation. For example, certain prior art approaches require the constant sensing of certain physiological changes in the esophagus, such as changes in esophageal pH, to detect acid reflux and/or esophageal motility and, based on such sensed changes, initiating or terminating an electrical stimulation to instantaneously close or open the LES, respectively, thereby avoiding an acid reflux episode. Other prior art approaches require continuous stimulation with sensing for swallow and stopping stimulation to allow for normal swallow to happen. This creates a complex device and has not proven to be feasible or effective in practice.

Therefore, there is still a need for a safe and effective method of treatment that can help alleviate symptoms of GERD in the long term, without adversely affecting the quality of life of the patients. In particular, there is a need for simple, efficient GERD device and treatment methods that does not inhibit a patient from swallowing and do not rely on an instantaneous response from the patient's LES to avoid episodes of acid reflux. There is a need for treatment protocols and devices which are programmed to implement such protocols, which can be easily programmed and do not require complex physiologic sensing mechanisms in order to operate effectively and safely. In addition, there is still a need for minimally invasive and effective treatment for obesity. Moreover, there is not only a need for better devices in stimulation based therapies, but there is also a need for a safe and minimally invasive method and system that enables easy and expeditious deployment of such devices at any desired location in the body.

It is further desirable to have a system for the treatment of GERD which includes a stimulator and an optional sensor adapted to be placed in a patient's LES tissue.

It is further desirable to have a system for the treatment of GERD which includes an active implantable medical device (AIMD) and temporary sensor adapted to be placed in a patient's GI lumen where the sensors are designed to naturally dissolve or pass out through the lumen and the AIMD is adapted to dynamically acquire, process, measure the quality of, and use sensed data only when the sensor is present.

It is further desirable to have a system for the temporary treatment of GERD which includes an AIMD, which is adapted to be placed in a patient's GI lumen, designed to naturally dissolve or pass out through the lumen, and is adapted to deliver electrical stimulation to tissue at or in the vicinity of the LES. Such temporary stimulation scheme can additionally be used for pre-screening of patients likely to benefit from permanent stimulation.

It would further be desirable for the stimulator to use periodic or occasional sensing data to improve the treatment of GERD by dynamically detecting when a sensor is present, determining when a sensor is transmitting, or capable of transmitting, data, and processing the sensed data using an application having a special mode which opportunistically uses the sensed data to change stimulation parameters.

It is also desirable to automate the setting or calibration of some or all device parameters in order to reduce the need for medical follow-up visits, reduce burdens on healthcare providers and patients, decrease the rate of programming mistakes, and improve outcomes, thereby improving the treatment of GERD.

SUMMARY

The present specification is directed toward a device, having a plurality of dimensions, adapted for placement proximate a patient's lower esophageal sphincter (LES) using endoscopic or laparoscopic or surgical techniques and programmed to treat esophageal dysfunction, comprising a stimulator enclosed within a housing and a plurality of electrodes wherein said electrodes are attached to the outer surface of the housing using conductors at least 1 mm in length. In one embodiment, the electrodes are adapted to be placed in a right or left anterior quadrant of the LES. In one embodiment, the housing comprises a needle having a length in the range of 5-50 mm and, more preferably, in the range of 10-25 mm, for creating a pathway for electrode implantation into the muscularis of the LES.

In one embodiment, electrodes are of sufficient length to allow them to be placed entirely within the LES. In another embodiment, the electrodes are of sufficient length to allow them to be placed proximate to the LES wherein the electrical field generated stimulates the LES.

In one embodiment, the device is at least 6 mm long and no more than 10 cm long to minimize fibrosis within peritoneal cavity.

In one embodiment, the device is adapted to be inserted into a laparoscopic trocar and has a diameter of greater than 6 mm but less than 25 mm.

In one embodiment, the device has an energy source that is rechargeable. In one embodiment, the device has a recharge frequency of no more than once per day for 6 hours. In one embodiment, the device has an energy source that is a battery that is a solid state battery, lithium ion battery, or super capacitor battery. In another embodiment, the device has an energy receiving unit anchored to an abdominal wall of the patient to maximize coupling between energy transmitting and receiving units. In another embodiment, the is not rechargeable and has an implant life of at least 1 year.

In one embodiment, the electrodes of the device are permanently attached to the housing by insulated conductors no longer than 65 cm. In another embodiment, the electrodes of the device are attached to the housing by insulated conductors which are detachable from the housing and are no longer than 65 cm.

In one embodiment, the device is adapted to be attached to an abdominal wall of the patient. In another embodiment, the device is adapted to be attached to the outer surface or serosa of a stomach wall of the patient.

In one embodiment, the device is adapted to be delivered and anchored through a single port laparoscopic procedure. In another embodiment, the device is adapted to be delivered and anchored using an articulated trocar in a laparoscopic procedure. In yet another embodiment, the device is adapted to be delivered into a peritoneal cavity of the patient through an incision that is created for a laparoscopic port.

The present specification is also directed toward a system for detecting eating by a patient, having a gastrointestinal tract, comprised of a transmitter and a receiver that communicate with each other, wherein the transmitter is placed within a portion of the gastrointestinal tract, wherein the receiver is placed within a portion of the gastrointestinal tract, wherein the transmitter and receiver are separated by a portion of the gastrointestinal tract, and wherein a modulation of the communication between the transmitter and receiver is monitored by a processor and used by the processor to determine if the patient has ingested a quantity of liquid, solids, or both.

In various embodiments, the transmitter is adapted to be placed on a portion of an abdominal wall of the patient, a portion of an esophagus of the patient, a portion of a lower esophageal sphincter of the patient, a portion of a cardia sphincter of the patient, or an outer anterior stomach wall of the patient.

In various embodiments, the receiver is adapted to be placed on a portion of an abdominal wall of the patient, a portion of an esophagus of the patient, a portion of a lower esophageal sphincter of the patient, a portion of a cardia sphincter of the patient, or an outer anterior stomach wall of the patient.

In one embodiment, modulation occurs when a distance between the transmitter and receiver is affected by an ingestion of liquid, food, or both.

In one embodiment, the distance between the transmitter and receiver is continuously measured to determine if liquid, food, or both is being ingested. In various embodiments, the distance is measured using ultrasonic waves, electric fields, magnetic fields, optical waves, or electro-magnetic fields.

The present specification is also directed toward a method for treating gastroesophageal reflux occurring within a patient comprising implanting within the patient a stimulation device having a stimulator enclosed within a housing and a plurality of electrodes attached in electrical communication with said stimulator wherein said electrodes are anchored in a position that is at least 1 mm and, more preferably, at least 5 mm, from the patient's cardiac tissue. In another embodiment, the electrodes are positioned at a distance at least ¼, and more preferably, greater than ½, the shortest distance between two electrodes, from the patient's cardiac tissue. In another embodiment, the electrodes are positioned such that the electric field is less than 75% of the maximum electric field between two electrodes.

In one embodiment, the stimulator has a plurality of anchor points and anchoring is performed by sutures or Nitinol suturing techniques. In another embodiment, the stimulator has a plurality of fixation points and fixation is performed by a plurality of clips.

The present specification is also directed toward a method for treating gastroesophageal reflux occurring within a patient comprising implanting within the patient a stimulation device having a stimulator enclosed within a housing and a plurality of electrodes attached in electrical communication with said stimulator wherein said electrodes are anchored in a position that is at least 1 mm and, more preferably, at least 5 mm, from the patient's main vagal trunk.

In one embodiment, the stimulator has a plurality of anchor points and anchoring is performed by sutures or Nitinol suturing techniques. In another embodiment, the stimulator has a plurality of fixation points and fixation is performed by a plurality of clips.

The present specification is also directed toward a method of treating gastroesophageal reflux disease (GERD) in a patient having a lower esophageal sphincter (LES) comprising: implanting a stimulation device proximate the LES wherein the stimulation device is programmable and provides electrical stimulation to the LES to produce a contraction of the LES; measuring a pH in the patient's esophagus and generating pH data; transmitting the pH data to a processor housed within a computing device external to the patient and storing the pH data within the computing device; electronically presenting the patient with questions relating to symptoms arising from the patient's GERD; electronically receiving answers from the patient; analyzing the pH data in relation to the answers to generate programming parameters; and programming the stimulation device using the programming parameters.

In one embodiment, measuring the pH comprises implanting at least one pH sensor in the esophagus proximate the LES wherein the pH sensor is configured to continually monitor the pH of the lower esophagus and is capable of transmitting sensed pH data. In one embodiment, the pH sensor is adapted to be implanted endoscopically.

In various embodiments, the questions include any one or more of questions relating to a timing of the patient's GERD symptoms, a duration of the patient's GERD symptoms, a severity of the patient's GERD symptoms, the patient's meal times, types of food ingested by the patient, types of liquid ingested by the patient, the patient's sleep times, and the patient's exercise regimens.

In one embodiment, programming of the stimulation device comprises changing at least one operational parameter, wherein the at least one operational parameter comprises stimulation start time, stimulation duration, and/or stimulation amplitude.

In one embodiment, the questions are electronically presented to the patient by communicating those questions through a network to a computing device in the patient's possession. In one embodiment, the computing device is a mobile phone.

In one embodiment, the pH data, programming parameters, and patient's answers are stored in a memory and in relation to a user account that is controlled by the patient and accessible using a network accessible computing device.

In one embodiment, the method of treating gastroesophageal reflux disease (GERD) in a patient having a lower esophageal sphincter (LES) further comprises providing an online service that electronically receives the pH data through a network and stores the pH data. In one embodiment, the online service electronically receives the patient's answers through the network and stores the answers. In one embodiment, the online service also electronically receives other data representing at least one physiological value wherein the physiological value includes at least one patient eating state, supine position, level of physical activity, or blood glucose level.

In one embodiment, the method of treating gastroesophageal reflux disease (GERD) in a patient having a lower esophageal sphincter (LES) further comprises using a remote process to automatically program the stimulating device after generating the programming parameters.

In one embodiment, the online service further electronically transmits reminders and/or recommendations to the patient regarding diet and exercise regimens. In one embodiment, the online service further electronically receives questions and appointment requests from the patient.

In one embodiment, the online service monitors the patient's compliance with at least one of a treatment, diet, or exercise regimen or scheduled appointment, determines a degree of compliance, and generates a reward for the patient based on the degree of compliance.

The aforementioned and other embodiments of the present invention shall be described in greater depth in the drawings and detailed description provided below.

DESCRIPTION OF THE DRAWINGS

The aforementioned and other embodiments shall be described in greater depth in the drawings and detailed description provided below.

DETAILED DESCRIPTION

Figure 1:
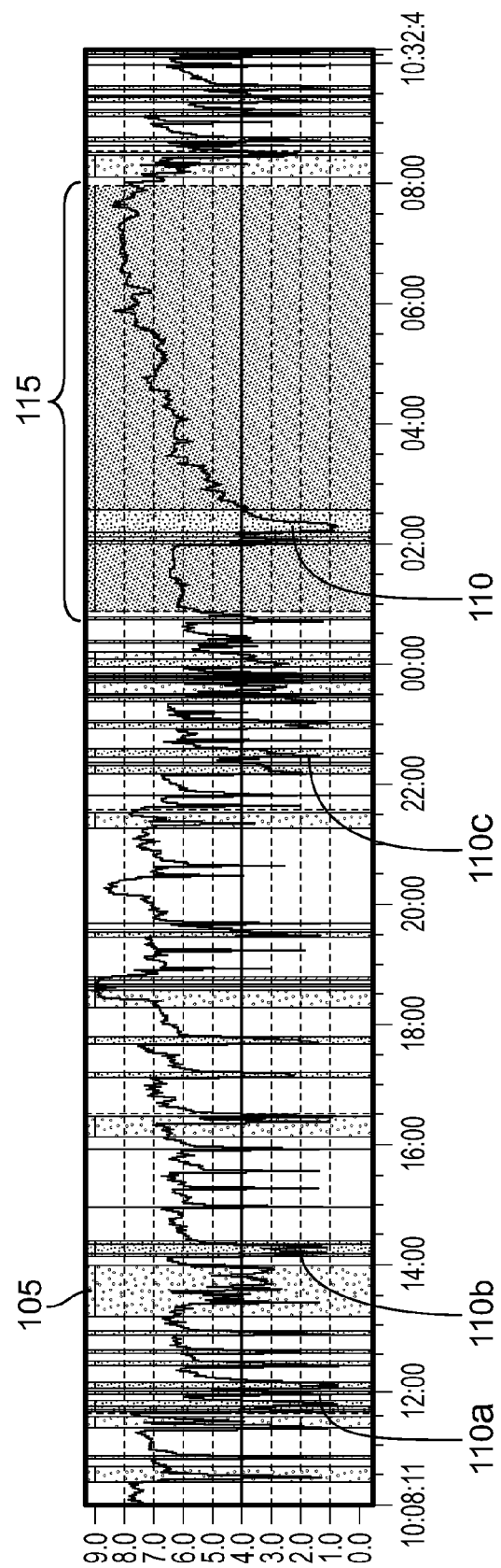
FIG. 1 is a first exemplary esophageal pH trace of a patient receiving non-specific LES electrical stimulation.

The present specification describes methods and systems for treating gastroesophageal reflux disease (GERD) by implanting an electrical stimulation device using laparoscopic or endoscopic techniques, capturing an eating event and detecting eating, using an implantable electrical stimulation device, enabling a patient to interface with an implanted stimulation device, and applying treatment processes. It should be appreciated that the methods and systems are being described with respect to specific embodiments, but are not limited thereto.

The present specification is directed towards multiple embodiments. The following disclosure is provided in order to enable a person having ordinary skill in the art to practice the claimed embodiments. Language used in this specification should not be interpreted as a general disavowal of any one specific embodiment or used to limit the claims beyond the meaning of the terms used therein. The general principles defined herein may be applied to other embodiments and applications without departing from the spirit and scope of the claimed embodiments. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that are known in the technical fields related to the claims have not been described in detail so as not to unnecessarily obscure the claimed embodiments.

It should be appreciated that the systems and methods described herein can be used with a plurality of different devices, including those electrical stimulation devices disclosed in U.S. Pat. No. 7,702,395, U.S. patent application Ser. Nos. 10/557,362 and 12/598,871, U.S. Pat. No. 6,901,295, PCT Application No. PCT/US08/56479, U.S. patent application Ser. Nos. 12/030,222, 11/539,645, 12/359,317, and 13/041,063, and PCT Application Numbers PCT/US09/55594 and PCT/US10/35753, which are herein incorporated by reference.

Devices Adapted to be Implanted Using Laparoscopic Surgical Techniques

In one embodiment, surgical or endoscopic techniques are used to implant an electrical stimulation device to treat GERD in a manner that is less invasive than those currently employed.

In one embodiment, an electrical stimulation device, or portions thereof, is adapted to be placed within or proximate the lower esophageal sphincter using laparoscopic surgical techniques and programmed to treat GERD, diurnal GERD, nocturnal GERD, and/or transient lower esophageal sphincter relaxation (tLESR). The outer surface of the device has electrodes attached thereto which comprise conductors at least 1 mm in length. The device may be a conventional pulse generator, a miniature pulse generator, or a microstimulator.

In one embodiment, the electrodes are adapted to be placed in the right anterior quadrant of the LES. In one embodiment, the electrodes are adapted to be placed the furthest possible distance from cardiac tissue while still being positioned to stimulate the LES. In one embodiment, the electrodes are positioned at least 1 mm and, more preferably, at least 5 mm from the patient's cardiac tissue. In another embodiment, the electrodes are positioned at a distance at least ¼, and more preferably, greater than ½ the shortest distance between two electrodes, from the patient's cardiac tissue. In another embodiment, the electrodes are positioned such that the electric field is less than 75% of the maximum electric field between two electrodes.

In one embodiment, the device has a plurality of structures or members which serve to anchor the device in the patient's tissue whereby the structures or members are configured to enable anchoring using sutures or nitinol suturing techniques.

In one embodiment, the device has a plurality of fixation points, structures, or members which serve to fix the device in the patient's tissue, preferably using clips.

In one embodiment, the device has at least one protrusion or needle for forming a pathway through a patient's tissue, where the pathway serves to enable electrode implantation into the muscularis of the patient's LES. In various embodiments, the protrusion or needle measures from 10-25 mm in length.

In one embodiment, the device comprises at least one electrode of sufficient length that allows the electrode to be placed entirely within the LES, without extending beyond the LES.

In one embodiment, the device is at least 1 cm long and no more than 10 cm long to minimize fibrosis within the peritoneal cavity.

In one embodiment, the device has a form factor, and is contained entirely within a housing, that can be inserted into a conventional laparoscopic trocar. The device has dimensions greater than 6 mm, but less than 25 mm, in diameter. In another embodiment, the device is physically configured and/or adapted to be delivered and anchored through a single port laparoscopic procedure. In another embodiment, the device is physically configured and/or adapted to be delivered and anchored using an articulated trocar in a laparoscopic procedure. In another embodiment, the device is physically configured and/or adapted to be delivered and anchored into the peritoneal cavity through an incision that is created and/or sized for a laparoscopic port.

In one embodiment, the device has a local energy source, such as a battery, that has one or more of the following characteristics: the energy source is rechargeable; has a recharge frequency of once per day for 6 hours, once per week for approximately 60 minutes, once per month, or once per year, comprises lithium ion battery technology, comprises solid state battery technology, comprises lithium polymer battery technology, comprises super capacitor technology; is not rechargeable, is not rechargeable and/or has an implant life of at least one year.

In one embodiment, the device comprises an energy receiving unit that is adapted to be anchored into the abdominal wall in order to maximize coupling between an energy transmitting unit and an energy receiving unit.

In one embodiment, the device has electrodes which are permanently attached by insulated conductors. In another embodiment, the electrodes attached to insulated conductors are detachable from the device.

In one embodiment, the device is adapted to be attached to the abdominal wall, on either the subcutaneous side or the peritoneal side, and/or adapted to be attached to the submucosa or outer surface or serosa of the stomach wall.

In one embodiment, the device is physically configured or adapted to be placed entirely within the submucosa adjacent to the LES.

In one embodiment, the device is adapted to be implanted within a patient such that the device is oriented between 45 degrees and 135 degrees within a standing patient in relation to a ground surface, which is at 0 degrees.

In one embodiment, the device comprises a plurality of electrodes which are adapted to be implanted such that they face the same LES muscularis.

Eating Detection Systems

In one embodiment, the present system is used to detect an eating event based upon an implanted transmitter and an implanted receiver, which are separated by a distance in a range of 0.5 cm to 20 cm, or preferably 1-2 cm. In one embodiment, the system comprises an implantable transmitter and receiver pair which are used to determine if a patient has ingested a quantity of liquid, solids, or both.

In one embodiment, the transmitter is adapted to be placed in or on the abdominal wall. In one embodiment, the transmitter is adapted to be placed on the outer anterior stomach wall, to be placed on the serosal surface of the stomach, to cross the LES, to cross the esophagus, or cross the cardia sphincter.

In one embodiment, the receiver is adapted to be placed in or on the abdominal wall. In one embodiment, the receiver is adapted to be placed on the outer anterior stomach wall.

In one embodiment, the transmitter and receiver are placed such that the distance between the transmitter and receiver is only modulated, changed, or otherwise affected by ingested liquid, food, or both. A controller monitors the distance between the transmitter and receiver. As the distance changes, the controller determines whether the distance change is indicative of whether a patient has ingested liquid, food, or both. In one embodiment, the distance between the transmitter and receiver is continuously measured to determine if liquid, food, or both is continuously being ingested. In one embodiment, the distance between the transmitter and receiver is continuously measured to differentiate if liquid, food, or both has been ingested.

The distance between the transmitter and receiver pair may be measured using ultrasonic sensors, electric field sensors, magnetic field sensors, electro-magnetic field sensors, and/or optical sensors.

Patient Interfacing Systems

In one embodiment, the system is adapted to be used to treat GERD using treatment algorithms and systems for collecting patient data, which are used to optimize treatment efficacy.

In one embodiment, the specification provides apparatuses and methods for collecting diet or lifestyle data from patients that are related to and are used to evaluate reflux events and/or GERD symptoms. Such data can be, for example, meal times, the type of food ingested, the type of liquid ingested, exercise regimens, sleep routines, as well as data related to time and severity of reflux symptoms.

The specification describes an apparatus used for said lifestyle data collection as well as storage and communication of said data. In one embodiment, the apparatus takes the form of a stand-alone device specially designed for this purpose. In another embodiment, the apparatus is an embedded component of a system used for health related purposes within the patient, such as a charger for an implantable device that includes lifestyle data collection and communication capabilities. In another embodiment, the apparatus includes software running on general purpose systems such as computers, smartphones, or other mobile devices. The device can be battery operated, portable, and handheld or have a desktop form factor using mains power. In another embodiment, such data is collected using paper diary and input into the external device by a health care professional and inputted into the device using wireless communication.

In one embodiment, the device performs multiple functions to enable the treatment of patients. For example, the device is adapted to be used for wireless charging of an implantable pulse generator (IPG) battery used as an energy source for an electrical stimulator for the LES. In another embodiment, the device can be integrated into a physician controlled computing device which is used in a clinic to wirelessly program the device parameters and which may also be used to collect patient input. Another example is that of a diagnostic pH monitoring device adapted to receive patient lifestyle data. Various combinations of the devices mentioned can be implemented and be interconnected using wireless or wired communication so that patient data is available when decisions are taken on parameter setting of the stimulation device.

In another embodiment, the device is programmable to implement changes in GERD treatment algorithms based on any patient data collected.

One objective of the device is to treat, prevent, or otherwise minimize inappropriate relaxations of the LES while allowing appropriate relaxations of the LES, such as for vomits, swallows, or burps. Another objective of the device is to stimulate the LES while not inhibiting normal physiological relaxations of the LES, such as for vomits, swallows, or burps. Another objective of the device is to reduce a patient's esophageal pH and/or modulate a patient's LES pressure while not causing a patient's cardia sphincter to completely close.

In some embodiments of the present specification, an apparatus for combining data from implantable sensors with patient input is used for optimizing GERD treatment algorithms. Preferably, a sensor generates a signal indicative of the swallowing of food and/or content thereof, providing information related to eating habits of the patient. An analysis module typically determines a quality of the food, for example, whether it is predominantly solid or liquid, and stores this information in an electronic memory. Alternatively or additionally, the analysis module determines other characteristics of the ingested material, for example, the nutritional, chemical, and/or caloric content. "Food," as used in the context of the present patent application and in the claims, is to be understood as including a bolus of solid food, a liquid, or both a solid food bolus and a liquid. "Swallowing," as used in the context of the present patent application and in the claims, is to be understood as being indicative of the onset of eating as defined by the contraction of musculature of the esophageal body and relaxation of the LES to pass food from the esophagus into the stomach.

In some embodiments of the present invention, swallowing is detected by tracking the electrical activity in muscle tissue in the stomach, in the esophagus or in other parts of the GI tract. Typically, the commencement of enhanced electrical activity is also detected in muscle tissue in the stomach. Measurement of the time delay between swallowing and the commencement of electrical activity in the antrum is typically used to differentiate between solid and liquid matter, which are generally passed at different rates through the stomach.

Alternatively or additionally, swallowing is detected by at least one sensor placed at a site on the gastrointestinal tract wherein the sensor generates a signal indicative of swallowing. Appropriate sites include, but are not limited to, a site on the esophagus, a site on the stomach, and a site on the throat.

Whenever detection of swallowing is described in the present patent application with respect to any specific sensor such as a sensor in the LES, it is to be understood as being by way of example, and not as excluding, detection by a sensor located elsewhere on the gastrointestinal tract.

Typically, electrical activity response criteria of the stomach of an individual patient are determined and calibrated by measuring the response of the patient's stomach to various types of solid and liquid food. To ensure appropriate compliance, calibration is typically performed under the supervision of a healthcare worker.

For some applications, various supplemental sensors are also applied to the gastrointestinal tract or elsewhere on or in the patient's body. These supplemental sensors, which may comprise pH sensors, blood sugar sensors, ultrasound transducers or mechanical sensors, typically convey signals to a control unit of the apparatus indicative of a characteristic of solids or liquids ingested by the patient. For example, an ultrasound transducer may be coupled to indicate whether ingesta are solid or liquid, and a pH sensor may indicate that an acidic drink such as tomato juice was consumed rather than a more basic liquid such as milk.

In some embodiments, the data collected from the patient is used to adjust the parameters of electrical stimulation applied to the lower esophageal sphincter with the intent of enhancing its tone using an implantable neuro-stimulating system.

In such applications the electrical stimulation is optimally delivered intermittently rather than continuously. Such intermittent stimulation is beneficial to preserve battery life of the implantable device and also to minimize the risk of physiological adaptation to the electrical stimulation that might reduce its efficacy over time or require increasing levels of energy to be delivered.

In another embodiment, the sensor is a pH sensor that records the pH data indicative of a reflux event and such data is used to design a stimulation algorithm to treat GERD. In this embodiment the stimulation could be programmed to be delivered a fixed time prior to such measured event to prevent future reflux events.

Adjusting Stimulation Time Based on Meal Times and Related Symptoms

In many GERD patients, there is significant association between food intake and symptoms. In some embodiments, the stimulation timing is adjusted manually or automatically to meal times so as to optimize efficacy of electrical stimulation of the LES in treating GERD.

Additionally, treatment algorithms take into account the unique association between stimulation session timing and the enhancement effect on the tone of the LES. Two important elements of this effect are critical in setting stimulation timing: latency effect and residual effect.

The latency effect means that the impact on tone is not immediate upon initiation of electrical stimulation but rather some time delay, typically between 5 minutes and one hour, needs to pass before the tone reaches optimal enhancement. In addition, the electrical stimulation is known to have a residual effect beyond the time of cessation of stimulation that typically lasts between 20 minutes and 6 hours but can last up to 24 hours. All of the above means that initiation of the stimulation session needs to start enough time before any potential meal time in order to "cover" the expected reflux events or symptoms following the meal.

In order to tailor the stimulation time to eating habits of different patients and to the changes of eating habits of each patient over time, some embodiments use patient input and/or data from physiological sensors.

Utilization of Patient Input

In a preferred embodiment the patient input data includes answers to the following exemplary questions:

1. At what times do you start your three most important meals of the day (three can vary from 1-8)
2. When you have GERD symptoms, do they usually— mark one answer:
   (a) follow meals?
   (b) happen during night time or when you lay down?
   (c) occur both when you lay down and after meals?
   (d) occur at a specific time of the day unrelated to meals or body position?
3. What times of day do you typically feel reflux symptoms (allow 2-6 answers)?

The answers to the above questions can typically be used as follows: If the answer to Q2 is (a) or (c), then specific stimulation sessions are programmed to start prior to, or in proximity to, the start of meals associated with symptoms. Setting the timing of stimulation to the earliest reported start of the meal is beneficial because of the known latency effect of electrical stimulation on LES tone. The latency period is between about 15 minutes to one hour so a preferred embodiment will program stimulation session to start one hour before the earliest reported time of meal start.

Answers to the questions above should be preferably obtained before the first time stimulation parameters are set and then be verified occasionally or as patients habit change.

An exemplary stimulation algorithm may include sessions 30 minutes before each meal, when a supine position is detected and specific times prior to reported GERD events. However, in a patient with erratic lifestyles, the total number of daily sessions can be equally spaced during the day such as every 2 hours or every 4 hours. In another embodiment, based on predominant upright reflux or predominant supine reflux, more sessions could be programmed for the upright or supine period, respectively.

Utilization of pH Input in Conjunction with Patient Input

In a preferred embodiment, acid exposure traces (pH esophageal traces) from the subject are also used in conjunction with the meal diary of the subject, if available, to determine optimal treatment. Such traces are used as follows:

1. Meal times indicated on the pH traces are used in combination with meal periods reported by the patient on the patient communication system. Such combination can be performed so that meal times from both sources are super-imposed and the combined set of meal times is used in the same way as a patient diary to adjust stimulation times.
2. Acid exposure events are analyzed so that time relations to various patient conditions (as indicated on the pH trace) are noted. Such conditions can be meal times, supine position and reported symptoms.

In a preferred embodiment, the acid exposure events are used in different stages of the patient treatment cycle to optimize treatment as follows:

During the pre-treatment stage, acid exposure times indicate if the patient has a tendency to reflux following meals, during sleep or both, serving as a validation to the patient questionnaire as described. Such validation is used in some embodiments to adjust parameters so that if at least one of the following conditions is fulfilled, then supine stimulation is programmed in the IPG: (a) patient questionnaire reports supine symptoms (b) in more than 0-5% of supine time acid exposure is noted in the pH trace or (c) any esophageal pH event is associated with patient symptom.

During the patient treatment stage, if a patient reports GERD symptoms, sub-optimal improvement in GERD and/or symptoms appearing in specific times, then the questionnaire is repeated and parameters adapted as necessary. The pH traces indicate times during which treatment is not optimal and therefore an enhanced stimulation regime is required. The pH traces are further used to prescribe the said treatment enhancement where as acid exposure events are first related to patient reports or other external information such as meal times, supine time, exercise time etc. and a stimulation session is added about one hour prior to the expected acid exposure event or preferably adjustable between 5 minutes and two hours before an expected reflux event. The pH trace can be related to the patient questionnaire in the following way: If an acid event is detected at a certain time and a meal is indicated about 0-2 hours prior to that event, then the patient is asked about the earliest time that such a meal is typically started so that the enhanced treatment addresses not only the events of the specific day of the test but also the variable meal times that the patient reports.

An example of using a combination of patient reports and pH traces for treating a patient is described. The patient is a GERD patient that presented with high acid exposure and GERD symptoms prior to treatment. The patient was implanted with an IPG that was programmed to deliver stimulation irrespective of patient meal times and symptom times of acid exposure periods. During the first two weeks of treatment, the patient received a stimulation session at 2 pm, at the time at which the device detected sleep (using an accelerometer that sensed when the patient had decreased motion and was in a supine posture for at least 30 minutes), and 8 hours following the sleep detection using the above algorithm.

Following two weeks of treatment, the patient was still complaining of GERD symptoms with only a small improvement compared to baseline. At week 2, the patient was questioned about eating habits and his pH trace was reviewed so as to adjust the stimulation times. The patient was reporting meals at about 2 pm, which was verified in his baseline pH trace. The pH trace also showed a short meal at 4:30 pm. The patient also complained of symptoms between 5 and 6 pm so a 4 pm stimulation session was added. Finally, a 6 pm stimulation was added to address post dinner symptoms. At week 4, the patient was questioned again about symptoms and this time a dramatic improvement was noted. The pH exposure trace on the current stimulation algorithm confirmed an improvement or normalization of esophageal acid exposure.

Additional patients underwent similar processes with similar results, demonstrating the importance of tailoring stimulation time to precede meals and other events that are precursors of pH exposure and GERD symptoms.

Referring to FIG. 1, an esophageal pH trace of the patient is shown wherein the shaded periods 105 indicate meal times and wherein areas with esophageal pH<4 are considered abnormal acid exposure periods 110. The X-axis is time of day and the Y-axis is the pH at each given time. As shown, the patient presents with many events of acid exposure mainly post meals (e.g. post 11 am breakfast 110a, post 1-2 pm lunch 110b and post 9:30 pm dinner 110c) as well as during night time (supine time 115 marked as time between about 1 am and 8:30 am). Total acid exposure is 10.4% of the time, which is considered abnormal (4% is the threshold for normal exposure). Such high acid exposure can result in various issues such as GERD symptoms, esophagitis, or Barrett's esophagus.

Figure 2:
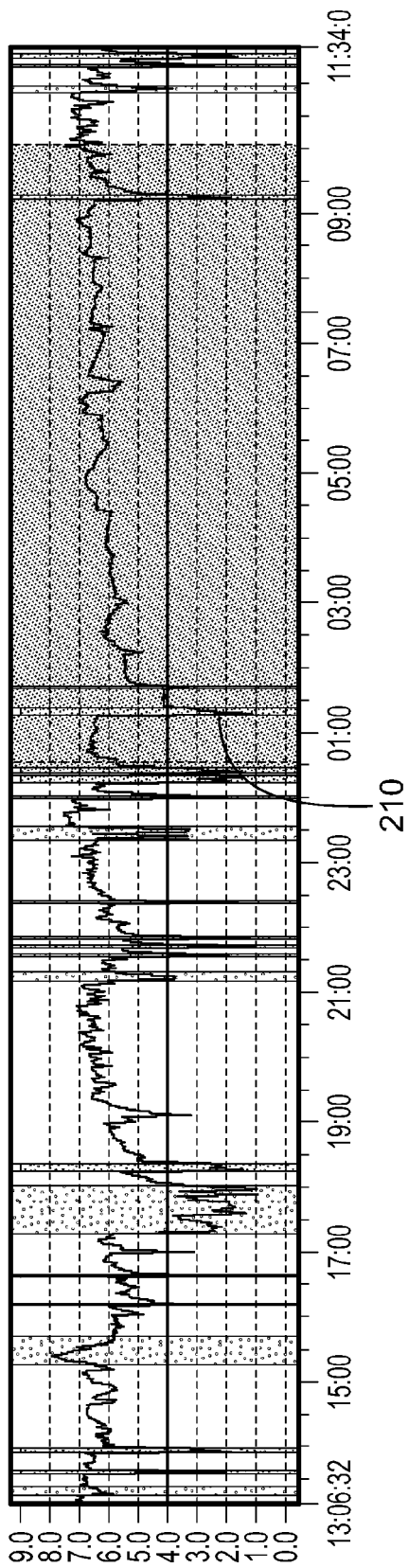
FIG. 2 is a second exemplary esophageal pH trace of the same patient receiving LES electrical stimulation therapy following the implantation of a patient specific optimization.

Referring to FIG. 2, an esophageal pH trace of the patient is shown after the patient, whose trace is shown in FIG. 1, has been treated with electrical stimulation using the patient specific algorithm for 4 weeks. The trace demonstrates that the majority of the esophageal acid exposure periods 210 are prevented and the esophagus acid exposure decreased to only 3.6% of the recording time, which is considered normal.

Methods and Utilities Related to a Patient Communication Device

The following will describe a new component of the GERD treatment that can utilize patient input, communicate with the implantable pulse generator (IPG) and/or communicate externally with a clinic or other service provider. Such an apparatus, namely a "patient communication device", can preferably include a processing unit that can integrate and analyze patient input with or without additional data as described above, such as pH data, and integrate the data to form a treatment recommendation in the form of stimulation session times, amplitudes, duration, etc. The patient communication device operates via an online service in which a patient can access his key physiological data and answer questions, such as those on the patient questionnaire that will help existing or new doctors program the patient's IPG. Use of the patient communication device frees the patient from being tied to one particular doctor and prevents the patient from being in a situation where they need treatment adjustment but don't have access to their data.

In one embodiment, any computer running the appropriate software and having online access can function as a patient communication device. Additionally or alternatively, the patient communication device can be a smart phone or other mobile device running the software so that the patient can use it without a need for a computer.

Figure 3:
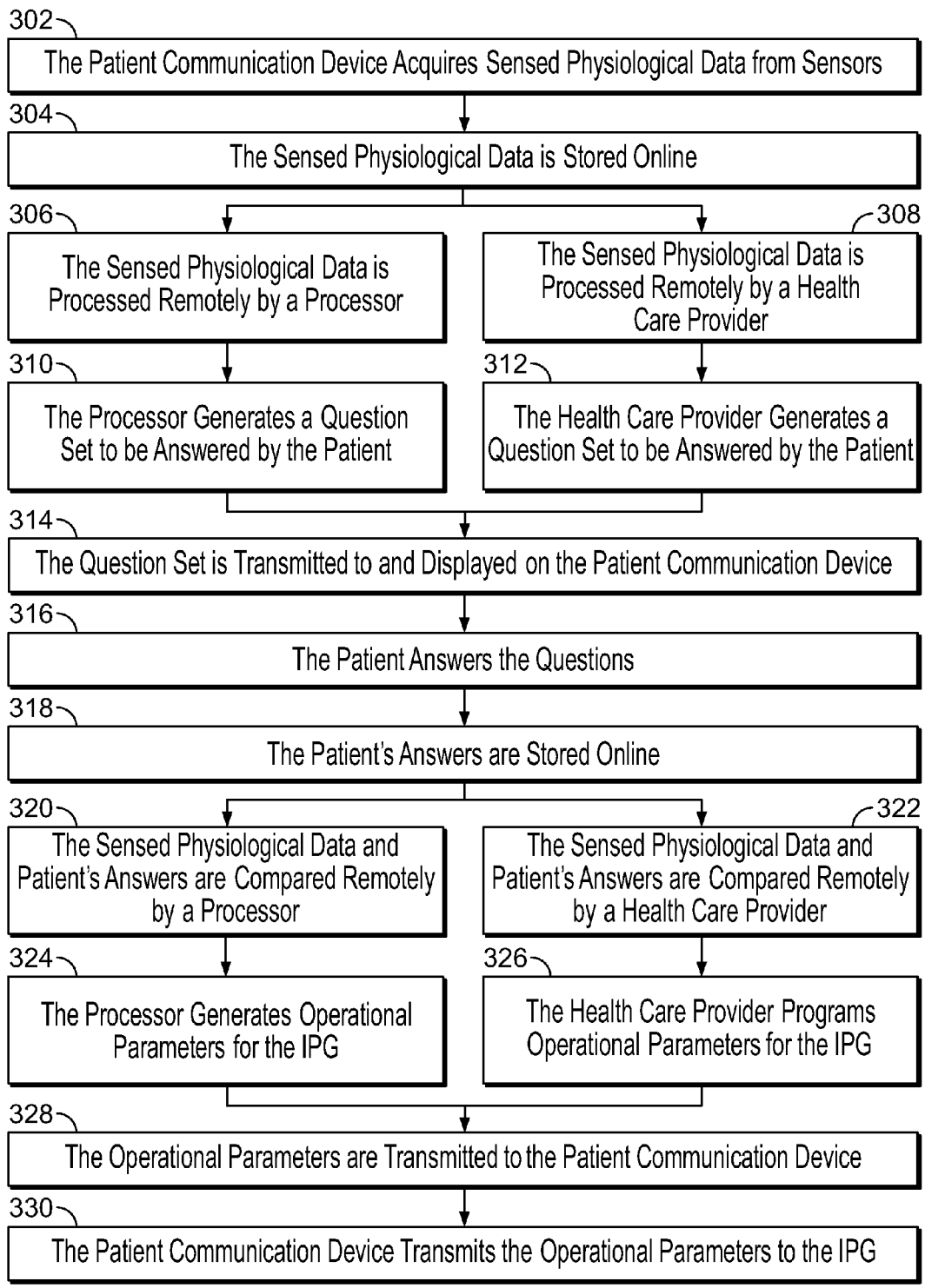
FIG. 3 is a flowchart detailing one process for optimizing the operational parameters of a patient device; and, FIG. 4 is a flowchart detailing another process for optimizing the operational parameters of a patient device.
Figure 4:
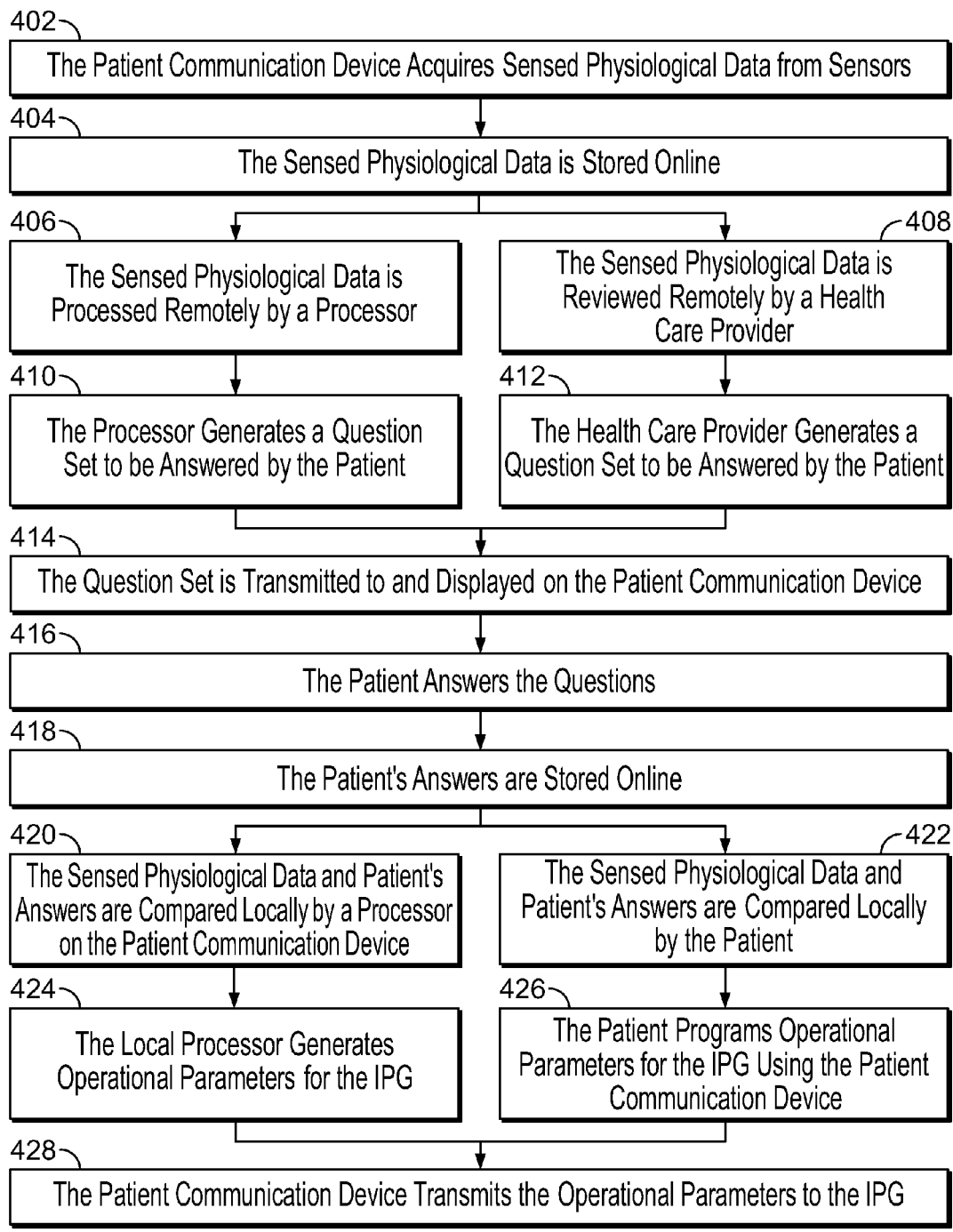

FIGS. 3 and 4 are flowcharts describing exemplary embodiments of different methods by which the online service and patient communication device operate to tailor GERD therapy for a specific patient. At steps 302 and 402, the patient communication device acquires sensed physiological data from sensors within the patient and, in steps 304 and 404, stores the data online using cloud based storage. The stored data is reviewed by a processor at steps 306 and 406 or a health care provider in a clinic or hospital setting at steps 308 and 408. In various embodiments, the sensed physiological data includes any one or more of esophageal pH, stomach pH, ingestion of food (using distance sensors as described above), supine position, patient weight, patient physical activity, and blood glucose level.

Using the sensed physiological data as a basis, either the remote processor at steps 310 and 410 or the health care provider at steps 312 and 412, generates a set of questions designed to further modify the GERD therapy. In various embodiments, the questions include any one or more of those in the questionnaire and questions regarding timing of reflux symptoms, duration of reflux symptoms, intensity of reflux symptoms, meal times, types of food ingested, types of liquid ingested, sleep times, and exercise regimens. At steps 314 and 414, the online service transmits the question set to the patient communication device which then presents it to the patient. At steps 316 and 416, the patient answer the questions directly on the patient communication device and the answers are stored in the cloud based storage at steps 318 and 418. The answers are also reviewable by a remote processor or a health care provider in a clinic or hospital setting.

In one embodiment, as shown at step 320 in FIG. 3, a processor located at the clinic or hospital automatically compares the sensed physiological data and the patient's answers and at step 324 automatically generates a set of operational parameters for the IPG specific to the patient's data. In another embodiment, as shown at step 322, a health care provider reviews the data and patient answers and then at step 326 programs operational parameters for the IPG. In another embodiment, as shown in step 420 in FIG. 4, a processor is located within the patient communication device automatically compares the sensed physiological data and the patient's answers and at step 424 automatically generates a set of operational parameters for the IPG specific to the patient's data. In yet another embodiment, as shown at step 422, the patient compares the data and his answers and at step 426 programs the IPG using the patient communication device. In various embodiments, the operational parameters include any one or more of stimulation start times, stimulation duration, and stimulation amplitude.

The generated or programmed operational parameters are then transmitted to the IPG. When the operational parameters are generated remotely by a processor or programmed remotely by a health care provider, said parameters are transmitted by the online service to the patient communication device at step 328, which then transmits the parameters to the IPG at step 330. When the operational parameters are generated locally by a processor on the patient communication device or are programmed by the patient using the patient communication device, then the patient communication device transmits said parameters directly to the IPG at step 428.

In a preferred embodiment, the patient questionnaire is applied using a patient communication device, being convenient for the patient as well as facilitating electronic data collection and analysis. Accessing the questionnaire is done via a web page to which patients log-on with a code from anywhere and the data will be transferred to the treating clinic electronically through an electronic database utilizing cloud based storage that is accessible by the clinic. In one embodiment, information relating to the patient, including the pH data, programming parameters, and patient's answers, is stored in the memory and in relation to a user account that is controlled by the patient and accessible using a network accessible computing device. Patient data will be protected from unauthorized access by standard web site protection tools such as SSL/HTTPS.

In a preferred embodiment, the clinic can communicate with the patient through the patient communication device. There can be various uses for such a communication channel, such as patient periodic reminders advising him/her to log in and answer the questionnaire. The means of communications can be standard, such as emails or instant phone messages, or can use special software and/or communication interfaces. When the patient uses a mobile application, the entire communication between the patient and the clinic can take place through the mobile application including patient reminders, questionnaire answering and data transfer to the clinic. The clinic can use the application or the other communication channels used for patient reminders to send him other relevant material such as medication information, scheduling of the next clinic visit, diet recommendations, and advice on various products and services that can be determined based on the patient profile stored in the clinic whereas such profile can be adapted from time to time based on the data communicated by the patient. The patient communication channel can be used for collecting additional medical information from the patient that can be used as initial screening information and may trigger (possibly in conjunction with physician review) scheduling in-person visits and specific tests.

In another preferred embodiment, the patient communication device can be centered around a patient charger that is used by the patient to wirelessly charge an implantable IPG with a rechargeable battery. Such a charger can have a screen for displaying patient messages and a keyboard for keying in information by the patient. It can also serve as a way station that can have a communication channel (wireless or wired) with a cell phone or a computer connected to the web to serve as a user interface, communication channel or both.

In embodiments in which the patient communication device can also establish a communication channel with the IPG, it can be adapted to configure or adjust the stimulation parameters to treat GERD of the subject. The patient communication device is adapted to monitor, using the received data, information regarding the applied stimulation, the information selected from the group consisting of: an amount of time per day that the implantable control unit drives the stimulator to apply the stimulation to the GI tract, and a number of times per day that the implantable control unit drives the stimulator to apply the stimulation to the patient and the time of day thereof.

For some applications, the patient communication system includes an output element, which is adapted to output the information regarding the applied stimulation. In a preferred embodiment, the GI tract includes the lower esophageal sphincter (LES) of the subject, and the one or more sensors are adapted to generate the respective sensor signals responsively to the GI tract physiological parameter of the esophagus and/or LES. For some applications, the patient communication device is adapted to monitor changes in the electrical properties of the esophageal tissue indicative of swallowing and/or the content of each swallow. Such electrical properties can include, for example, sensing of electrical action potentials and/or changes in the tissue impedance. In some embodiments, a gastric slow wave rate of the subject can be used as indicative of digestive state to improve the analytical capabilities of the system.

In one embodiment, the IPG is adapted to store data using patient input. The data is recorded using the accelerometer in the IPG. The patient can communicate the information to the IPG by simply tapping on the IPG and the tapping is recorded by the accelerometer. In this embodiment, the number or intensity of taps could represent a specific event. For example, one tap on the device may indicate start of a meal event, while two taps may indicate start of a reflux event. The event data can be recorded for download by the clinic to modify the stimulation algorithm or can be used by the IPG directly to modify the stimulation algorithm without input of a health care provider. The information gathered by the IPG will continuously modify the patient's lifestyle and GERD profile and adjust the stimulation algorithm to address the changing patient profile.

In another embodiment, an external device is used which produces a vibration with a characteristic that is specific to the event. The patient will place this device on the site of the IPG implant and press a specific event button on the external device which will then vibrate with the characteristic specific to the event. The vibrations are transmitted through the human tissue to the IPG which registers the specific event. The event data can be recorded for download by the clinic to modify the stimulation algorithm or can be used by the IPG directly to modify the stimulation algorithm without input of a health care provider. The information gathered by the IPG will continuously modify the patient's lifestyle and GERD profile and adjust the stimulation algorithm to address the changing patient profile.

In another embodiment, the IPG is adapted to store information regarding eating habits of the subject as detected by the swallowing sensors. For some applications, the IPG includes an output element, which is adapted to output the eating habit information. For some applications, the patient communication device is adapted to integrate and verify patient answers to the questionaires with the eating detection data received from the IPG. The patient communication device can be adapted to transmit the integrated eating habit information to the clinic via the communication channel.

For some applications, the patient communication device is adapted to receive, analyze and integrate indication of non-GI tract physiological parameters. Such parameters can include an indication of a weight of the subject, level of physical activity of the patient, blood glucose of the patient, etc. The patient communication device can generate a message to the IPG for adjustment of parameters and/or a transmission of the information to the clinic.

For some applications, the IPG is adapted to modify a parameter of the stimulation at least in part responsively to the information. For example, the stimulation parameter may include an intensity of the stimulation, and the IPG is adapted to modify the intensity of the stimulation at least in part responsively to the information, and/or the stimulation parameter may include a timing parameter of the stimulation, and the IPG is adapted to modify the timing parameter of the stimulation at least in part responsively to the information.

In an embodiment, the patient communication device is adapted to be coupled to a remote service provider. In one embodiment, the remote service provider can analyze the patient data, for example, pH and symptom data, and convert it into parameter setting changes recommended for a given patient, thereby making the work of the clinic easier and shorter. For some applications, the apparatus includes an external cradle, and the patient communication device is adapted to be removably coupled to the cradle, and to be coupled to the service provider via the cradle. For some applications, the patient communication device is adapted to receive information from the service provider. Alternatively or additionally, the patient communication device is adapted to send information to the service provider selected from the group consisting of at least a portion of the received data and information derived from an analysis of at least a portion of the received data.

In an embodiment, the patient communication device is configured to serve as a charger for the IPG. In such a case, the patient communication device includes a power source, and is adapted to drive the power source to wirelessly transfer energy via one or more transducers, and the implantable pulse generator includes a rechargeable battery, and is adapted to receive the transmitted energy, using one or more transducers, and charge the battery using the energy.

In one embodiment, the patient communication device is adapted to be located remotely from the subject. In such an embodiment, the patient communication device is not capable of recharging the IPG. Data is transmitted between the patient communication device and the IPG via RF communication at a distance of up to 3 meters. In another embodiment, the patient communication device is adapted to be located proximate the subject.

In another embodiment, the patient communication device is adapted to be coupled wired or wirelessly to a point-of-sale terminal. In one embodiment, the online service monitors the patient's compliance with the recommended treatment, diet, or exercise regimen or scheduled appointment, determines a degree of compliance, and generates a reward for the patient based on the degree of compliance. In an embodiment, generating the reward includes providing a financial incentive to the patient. In one embodiment, providing the financial incentive is based on a measure of successful responses to the clinic communication requests. In various embodiments, the financial incentive comprises any one or more of the following: refunding to the patient a portion of the purchase price of the device/and or software; providing a discount to the patient on routine medical care; and, providing a free device charging session for rechargeable devices.

For some applications, a method includes sending a reminder from the service provider to the site, and communicating the reminder to the subject. In an embodiment, the method includes analyzing, at the service provider, the eating-related information. For some applications, analyzing the eating-related information includes developing a recommendation based on the eating-related information, sending the recommendation from the service provider to the site, and communicating the recommendation to the subject from the site. For example, the recommendation may be selected from the group consisting of a recommended food and a recommended recipe. For some applications, the recommendation is commercial in nature.

For some applications, receiving of data from the IPG includes logging the data, and providing the financial incentive includes providing the financial incentive responsively to the logged data.

In an embodiment, providing the financial incentive includes providing the financial incentive in response to determining, responsively to the data, that the subject has followed a prescribed regimen. For some applications, the regimen includes a diet regimen intended to improve GERD symptoms, and providing the financial incentive includes providing the financial incentive upon determining, responsively to the data, that the subject has adhered to the prescribed diet regimen. Alternatively or additionally, the regimen includes an exercise regimen, and providing the financial incentive includes providing the financial incentive upon determining, responsively to the data, that the subject has adhered to the prescribed exercise regimen.

For some applications, functionality described herein with respect to a patient communication device is embodied that can communicate with a stationary or portable receiving device located in the clinic and is configured to collect data from the patient communication system.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of treating gastroesophageal reflux disease (GERD) in a patient having a lower esophageal sphincter (LES) comprising:
   implanting a stimulation device proximate the LES wherein said stimulation device is programmable and provides electrical stimulation to the LES to produce a contraction of said LES;
   measuring a pH in the patient's esophagus and generating pH data;
   transmitting said pH data to a processor housed within a computing device external to the patient and storing said pH data within said computing device;
   obtaining information relating to the patient's symptoms arising from the patient's GERD;
   analyzing said pH data in relation to said information to generate programming parameters; and
   programming said stimulation device using said programming parameters wherein said programming step comprises establishing fixed start times for initiating said electrical stimulation and fixed end times for terminating said electrical stimulation.

2. The method of claim 1 wherein measuring said pH comprises implanting at least one pH sensor in the esophagus proximate the LES wherein said at least one pH sensor is configured to continually monitor the pH of the lower esophagus and is capable of transmitting sensed pH data.

3. The method of claim 2 wherein said pH sensor is adapted to be implanted endoscopically.

4. The method of claim 1 wherein the information includes answers to any one or more of questions relating to a timing of the patient's GERD symptoms, a duration of the patient's GERD symptoms, a severity of the patient's GERD symptoms, the patient's meal times, types of food ingested by the patient, types of liquid ingested by the patient, the patient's sleep times, and the patient's exercise regimens.

5. The method of claim 1 wherein programming said stimulation device comprises changing at least one operational parameter, wherein said at least one operational parameter comprises stimulation start time, stimulation duration, and/or stimulation amplitude.

6. The method of claim 1 wherein the information is obtained by electronically presenting questions related to the patient's symptoms to the patient through a network to a computing device in the patient's possession and electronically receiving answers to said questions from said computing device.

7. The method of claim 6 wherein the computing device is a mobile phone.

8. The method of claim 6 wherein the pH data, programming parameters, and answers are stored in a memory and in relation to a user account that is controlled by the patient and accessible using a network accessible computing device.

9. The method of claim 1 further comprising providing an online service that electronically receives said pH data through a network and stores said pH data.

10. The method of claim 9 wherein said online service electronically receives the information through the network and stores said information.

11. The method of claim 9 wherein said online service electronically receives other data representing at least one physiological value and wherein said physiological value includes at least one patient eating state, supine position, level of physical activity, or blood glucose level.

12. The method of claim 1 further comprising using a remote process to automatically program said stimulating device after generating said programming parameters.

13. The method of claim 9 wherein said online service further electronically transmits reminders and/or recommendations to the patient regarding diet and exercise regimens.

14. The method of claim 9 wherein said online service further electronically receives questions and appointment requests from the patient.

15. The method of claim 9 wherein said online service monitors the patient's compliance with at least one of a treatment, diet, or exercise regimen or scheduled appointment, determines a degree of compliance, and generates a reward for the patient based on said degree of compliance.

16. The method of claim 1 further comprising providing a handheld patient input device, wherein said handheld patient input device is adapted to wirelessly charge said stimulation device.

17. The method of claim 16 wherein the handheld patient input device is adapted to monitor changes in tissue impedance.

* * * * *